United States Patent
Konno

(10) Patent No.: US 11,058,384 B2
(45) Date of Patent: Jul. 13, 2021

(54) IMAGE PROCESSING DEVICE, X-RAY CT DEVICE, AND IMAGE PROCESSING METHOD

(71) Applicant: Hitachi, Ltd., Tokyo (JP)

(72) Inventor: Yasutaka Konno, Tokyo (JP)

(73) Assignee: HITACHI, LTD., Tokyo (JP)

( * ) Notice: Subject to any disclaimer, the term of this patent is extended or adjusted under 35 U.S.C. 154(b) by 179 days.

(21) Appl. No.: 16/472,523

(22) PCT Filed: Dec. 4, 2017

(86) PCT No.: PCT/JP2017/043516
§ 371 (c)(1),
(2) Date: Jun. 21, 2019

(87) PCT Pub. No.: WO2018/154906
PCT Pub. Date: Aug. 30, 2018

(65) Prior Publication Data
US 2021/0128096 A1    May 6, 2021

(30) Foreign Application Priority Data
Feb. 27, 2017    (JP) .............................. JP2017-035186

(51) Int. Cl.
*A61B 6/00*    (2006.01)
*A61B 6/03*    (2006.01)

(52) U.S. Cl.
CPC ............ *A61B 6/5205* (2013.01); *A61B 6/032* (2013.01); *A61B 6/463* (2013.01); *A61B 6/482* (2013.01)

(58) Field of Classification Search
CPC ... G06T 2211/408; A61B 6/032; A61B 6/482; A61B 6/424; A61B 6/5205; A61B 6/463
See application file for complete search history.

(56) References Cited

U.S. PATENT DOCUMENTS

2008/0273666 A1*  11/2008  Walter ................... A61B 6/583
                                                        378/185
2016/0125565 A1    5/2016  Sulatycke et al.

FOREIGN PATENT DOCUMENTS

| JP | 2009153829 A | 7/2009 |
|----|--------------|--------|
| JP | 2014166351 A | 9/2014 |

(Continued)

OTHER PUBLICATIONS

International Search Report and Written Opinion for the International Patent Application No. PCT/JP2017/043516, dated Feb. 13, 2018, 7 pages.

(Continued)

*Primary Examiner* — Courtney D Thomas
(74) *Attorney, Agent, or Firm* — Baker Botts L.L.P.

(57) ABSTRACT

This is directed to calculating physical amounts of a plurality of types of basis materials without having to increase a calculation time.

An image processing device is provided which includes a first basis material transformation unit that calculates each of physical amounts of two or more basis materials included in a first basis material group based on two or more types of projection data different in energy distribution, an image generation unit that generates a plurality of images, each of which is at least one of a projection image and a reconstructed image of an object, from physical amounts of two or more basis materials included in the first basis material group, and a second basis material transformation unit that calculates a physical amount of a basis material included in a second basis material group which is different from the first basis material group based on the plurality of images.

8 Claims, 13 Drawing Sheets

(56) References Cited

FOREIGN PATENT DOCUMENTS

| | | |
|---|---|---|
| JP | 2014239840 A | 12/2014 |
| JP | 2016087468 A | 5/2016 |

OTHER PUBLICATIONS

International Preliminary Report on Patentability, dated Sep. 6, 2019, which issued during the prosecution of International Application No. PCT/JP2017/043516, which corresponds to the present application.

* cited by examiner

Fig.9
(A)
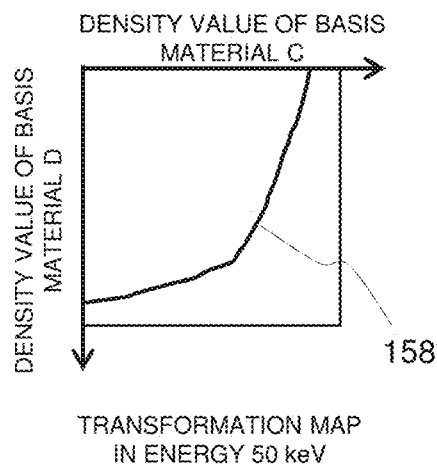
(B)
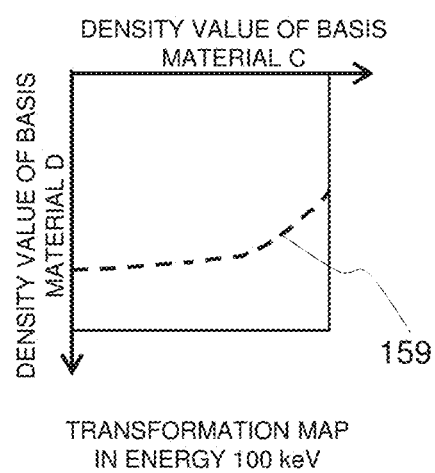
(C)
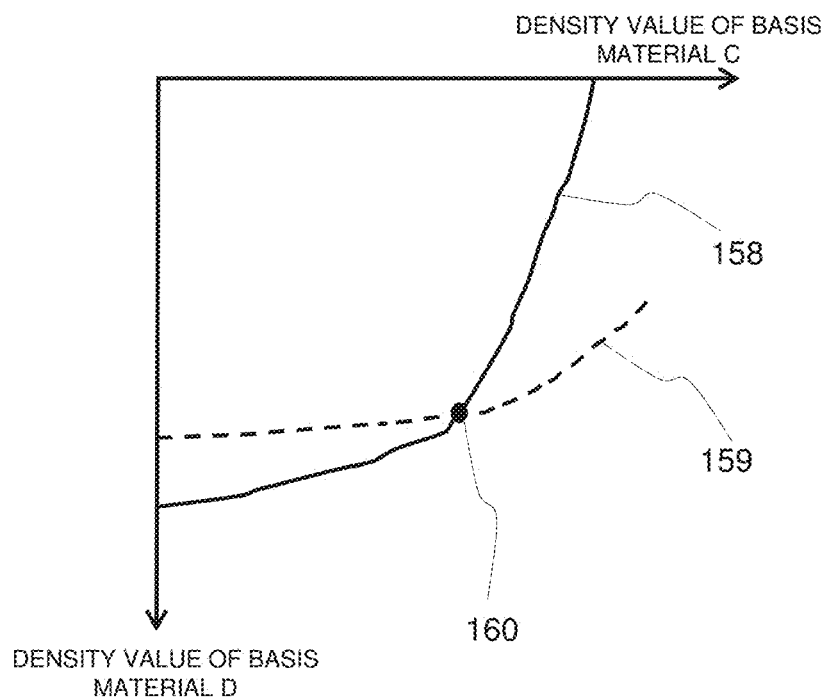

IMAGE PROCESSING DEVICE, X-RAY CT DEVICE, AND IMAGE PROCESSING METHOD

CROSS-REFERENCE TO RELATED APPLICATIONS

This application is a national phase claiming the benefit of and priority to International Patent Application No. PCT/JP2017/043516, entitled "IMAGE PROCESSING DEVICE, X-RAY CT DEVICE, AND IMAGE PROCESSING METHOD", filed Dec. 4, 2017, which claims priority to Japanese Patent Application No. 2017-035186, filed Feb. 27, 2017, which are hereby incorporated by reference in their entireties.

TECHNICAL FIELD

The invention as claimed in the present application relates to an image processing device, an X-ray CT device, and an image processing method and, more particularly, to an image processing device, an X-ray CT device, and an image processing method each of which performs image processing on data acquired by an X-ray detector of the photon counting type.

BACKGROUND ART

An X-ray CT device is a device that calculates X-ray absorption coefficients (linear attenuation coefficient) from projection data which is an X-ray transmission image of a subject under test photographed from a plurality of directions, and obtains a reconstructed image which is a tomographic image of the subject under test. While, previously, an X-ray CT device using an X-ray detector of the integration type as an X-ray detector for acquiring projection data has been mainly used, in recent years, an X-ray CT device equipped with an X-ray detector of the photon counting type, which measures the number of X-ray photons, has been being developed (for example, Patent Literature 1). This device is able to generate various reconstructed images, such as a virtual monochromatic image for every energy, which has not been able to be acquired by conventional X-ray CT devices, a reconstructed image representing a distribution of other than absorption coefficients, including, for example, a basis material density image, an effective atomic number image, an electron density image, a photoelectric effect image, and a Compton scattering image, and an absorption coefficient image in X-rays with an energy distribution of other than a spectrum used for photographing (hereinafter, these images being referred to as "multi-energy images").

Such a photon counting-type X-ray CT device is able to acquire projection data for every plurality of energy bins and obtain the physical amount of a basis material corresponding to an output value of the projection data with use of a transformation parameter such as a transformation map. The physical amount of a basis material as used herein is the length or surface density of the basis material in the case of projection data. Using the physical amount of a basis material enables generating various multi-energy images.

PRIOR ART LITERATURE

Patent Literature

Patent Literature 1: JP-A-2014-239840

SUMMARY OF THE INVENTION

Problems that the Invention is to Solve

However, the X-ray CT device of Patent Literature 1 requires transformation parameters to be provided for respective X-ray irradiation conditions, and further requires transformation parameters to be provided for respective combinations (sets) of basis materials. Accordingly, prior to photographing, it is necessary to previously determine a large number of transformation parameters corresponding to assumed X-ray irradiation conditions and combinations of basis materials with use of experiments or simulations, so that many processes are required. Then, a large storage capacity for storing many transformation parameters obtained in these processes becomes required. In the case of setting a plurality of types of basis materials to generate respective images, a larger number of processes and a larger storage capacity would be required.

Furthermore, the transformation of the physical amount of a basis material includes a method that is performed based on projection data and a method that is performed based on a reconstructed image. The method that is performed based on projection data is able to perform transformation in consideration of differences in characteristics of the respective X-ray detection elements and, therefore, has the advantage of being able to obtain the physical amount of a basis material with a high degree of accuracy.

However, if the transformation of the physical amount of a basis material is performed with use of the method that is performed based on projection data, some processing time is required, so that the method that is performed based on projection data is unsuitable for such processing as to set various basis materials to generate respective images.

On the other hand, the method that is performed based on a reconstructed image is not able to take into consideration differences in characteristics of the respective X-ray detection elements, but has the advantage of being able to perform processing at high speed.

The present invention has been made in view of the above-mentioned circumferences, and an object thereof is to calculate physical amounts of a plurality of types of basis materials without having to increase a calculation time and, eventually, to acquire desired images.

Means for Solving the Problems

To solve the above-mentioned problems, the present invention provides the following means.

An aspect of the present invention provides an image processing device including a first basis material transformation unit that calculates each of physical amounts of two or more basis materials included in a first basis material group based on two or more types of projection data different in energy distribution, an image generation unit that generates a plurality of images, each of which is at least one of a projection image and a reconstructed image of an object, from physical amounts of two or more basis materials included in the first basis material group, and a second basis material transformation unit that calculates a physical amount of a basis material included in a second basis material group which is different from the first basis material group based on the plurality of images.

Advantage of the Invention

According to the present invention, the physical amounts of a plurality of types of basis materials can be calculated without having to increase a calculation time, and desired images can be acquired.

BRIEF DESCRIPTION OF THE DRAWINGS

FIGS. 9(A) to 9(C) are examples of transformation maps which are used in the basis material calculation processing in the X-ray CT device with the image processing device according to the embodiment of the present invention applied thereto.

MODE FOR CARRYING OUT THE INVENTION

An embodiment of the present invention will be described with reference to the drawings.

An image processing device according to the present invention is an image processing device including a first basis material transformation unit that calculates each of physical amounts of two or more basis materials included in a first basis material group based on two or more types of projection data different in energy distribution, an image generation unit that generates a plurality of images, each of which is at least one of a projection image and a reconstructed image of an object, from physical amounts of two or more basis materials included in the first basis material group, and a second basis material transformation unit that calculates a physical amount of a basis material included in a second basis material group which is different from the first basis material group based on the plurality of images.

According to such an image processing device, since the physical amount of a basis material included in the second basis material group is calculated from images acquired based on the physical amounts of two or more basis materials included in the first basis material group, the physical amounts of a plurality of types of basis materials can be calculated without having to increase an image calculation time.

Hereinafter, the embodiment of the present invention is more specifically described.

Embodiment

Hereinafter, an X-ray CT device including an image processing device according to the embodiment of the present invention is described with reference to the drawings.

Figure 1:
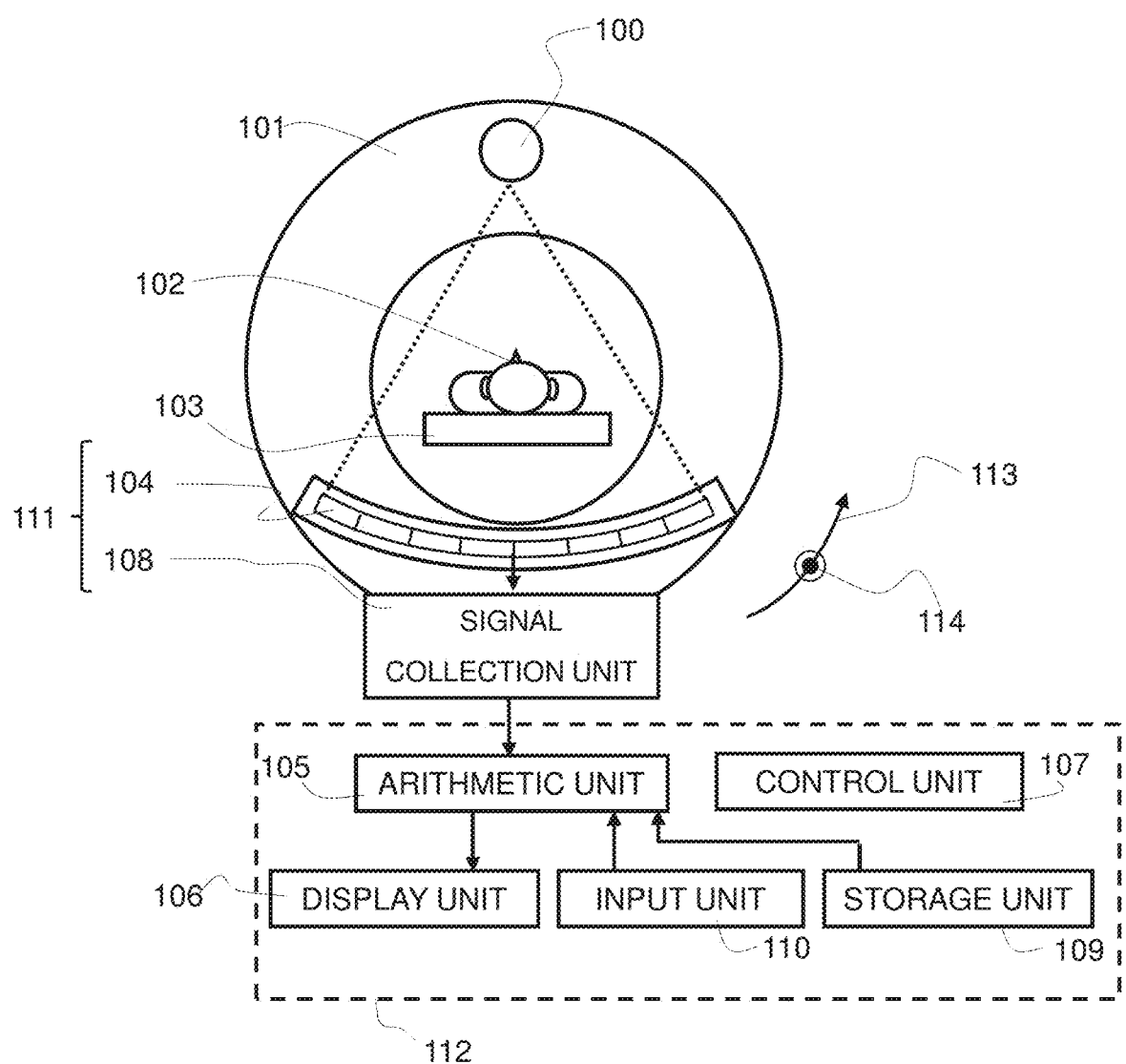
FIG. 1 is a block diagram illustrating an outline of an X-ray CT device with an image processing device according to an embodiment of the present invention applied thereto.

As illustrated in FIG. 1, the X-ray CT device includes an X-ray source 100, an X-ray detector 111, a gantry rotation unit 101, in which the X-ray source 100 and a detection unit 104 (described below) of the detector 111 are arranged opposite each other and which rotates around a predetermined rotation axis, and a bed top plate 103 located in an opening of the gantry rotation unit 101, which operate as a photographing system, and a signal processing unit 112, which processes a signal acquired by the X-ray detector 111 in conjunction with an operation of the photographing system.

The X-ray source 100 causes an electron beam accelerated by, for example, an X-ray tube voltage to collide with a target metal such as tungsten or molybdenum, thus generating X-rays from its collision position (focus).

The gantry rotation unit 101 contains the X-ray source 100 and the detection unit 104, which are arranged opposite each other, and rotates around a predetermined rotation axis. An opening into which a subject under test 102 is insertable is provided at the center of the gantry rotation unit 101, and the bed top plate 103, on which the subject under test 102 is allowed to lie, is located in the opening. The bed top plate 103 and the gantry rotation unit 101 are configured to be able to move relative to each other along a predetermined direction.

The X-ray detector 111 includes the detection unit 104, in which a plurality of X-ray detection elements of the photon counting type that detects incident X-ray photons and performs counting thereof while discriminating between a plurality of (for example, three) energy ranges is arranged, and a signal collection unit 108, which collects projection images output from the X-ray detection elements. Details of the detection unit 104 are described below.

The signal processing unit 112 includes an arithmetic unit 105, a display unit 106, a control unit 107, a storage unit 109, and an input unit 110.

Figure 2:
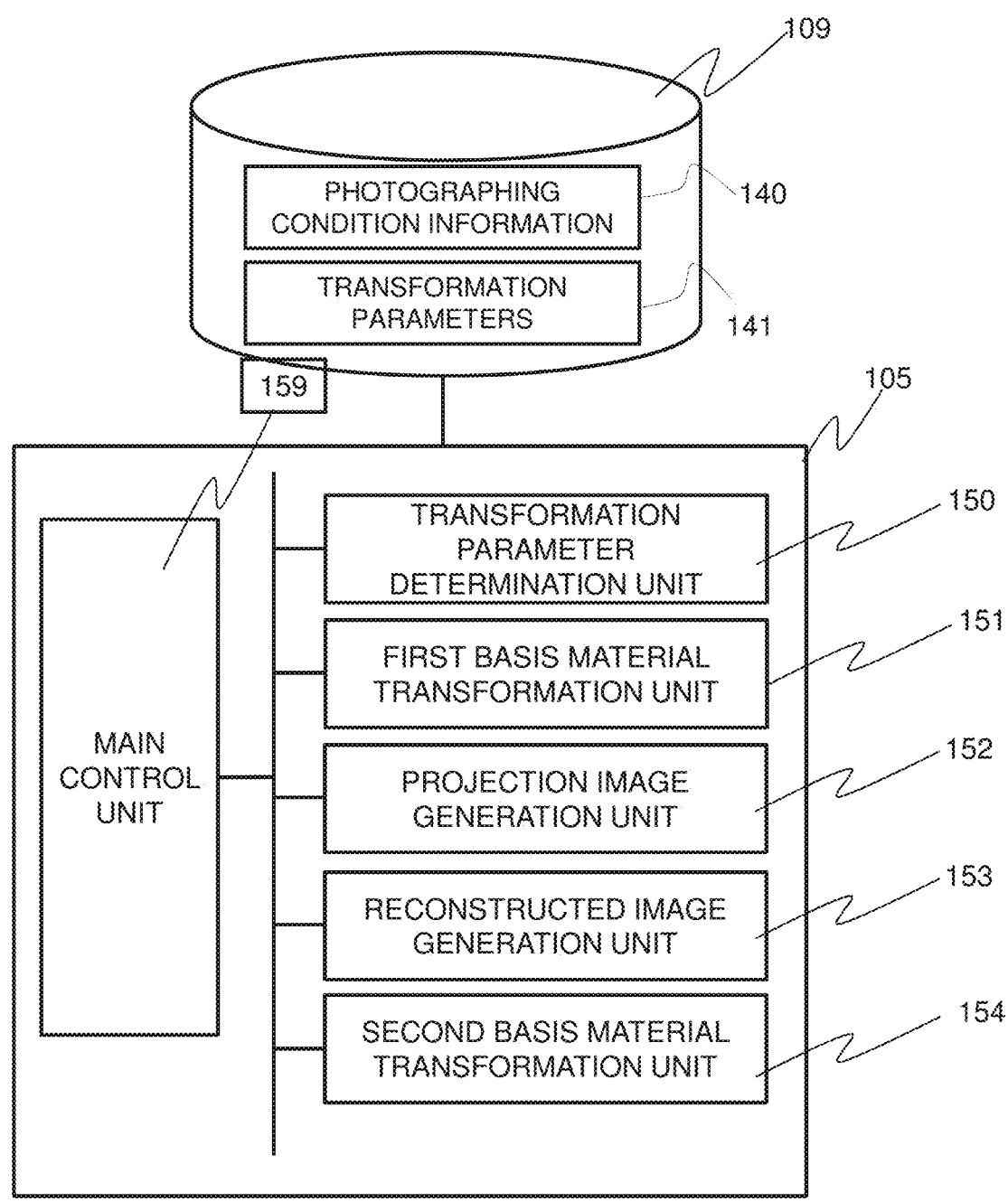
FIG. 2 is a block diagram illustrating an outline of an arithmetic unit in the X-ray CT device with the image processing device according to the embodiment of the present invention applied thereto.

As illustrated in FIG. 2, the arithmetic unit 105 includes a transformation parameter determination unit 150, which determines a transformation parameter for use in basis material transformation with respect to the signals collected by the signal collection unit 108 so as to perform predetermined arithmetic processing on the collected signals, a first basis material transformation unit 151, which obtains the physical amounts of a plurality of basis materials included in a first basis material group, a projection image generation unit (image generation unit) 152, which generates a projection image from the physical amount of a basis material included in the first basis material group, a reconstructed image generation unit 153, which performs reconstruction processing to generate a reconstructed image such as a multi-energy image, a second basis material transformation unit 154, which calculates the physical amount of a basis material belonging to a second basis material group from the projection image generated by the projection image generation unit 152 or the reconstructed image generated by the reconstructed image generation unit 153, and a main control unit 159, which controls the above units.

The arithmetic unit 105 performs various arithmetic operations based on information or transformation parameters stored in the storage unit 109. The arithmetic unit 105 reads out, for example, various pieces of information or parameters from the storage unit 109 as needed, and performs arithmetic operations, such as signal processing, image processing, and image reconstruction.

The display unit 106 displays a user interface screen (details thereof being described below), which enables the user to enter various inputs, or displays, for example, a multi-energy image generated by the arithmetic unit 105.

The control unit 107 includes an X-ray control unit, which controls an operation of a generation drive source of the X-ray source 100, a readout control unit, which controls a signal readout operation of the X-ray detector 111, a photographing control unit, which controls rotation of the gantry rotation unit 101 and shifting movement of the bed top plate 103, and an entirety control unit, which controls the entirety of these units.

The storage unit 109 stores, for example, parameters or data for use in arithmetic processing in the arithmetic unit 105 and a photographing condition used to acquire projection data. Specifically, for example, photographing condition information 140, which is used for basis material transformation, and transformation parameters 141, which are used to obtain the physical amounts of basis materials, are included in the stored information or data. For example, transformation maps are stored as the transformation parameters which are used to calculate the physical amounts of basis materials.

The input unit 110 performs inputting of, for example, a photographing condition in the X-ray CT device.

A part or the whole of the arithmetic unit 105 and the control unit 107 can be constructed as a system including a central processing unit (CPU), a memory, and the main storage unit 109, and the function of each unit constituting the arithmetic unit 105 and the control unit 107 can be implemented by the CPU loading a program previously stored in the storage unit 109 onto the memory and executing the program. Moreover, a part or the whole of the function can be configured by hardware, such as an application specific integrated circuit (ASIC) or a field programmable gate array (FPGA).

In the following description, unless otherwise described, the elements constituting the above-mentioned photographing system, the control unit 107, and the signal processing unit 112 have configurations similar to those of elements included in a publicly known X-ray CT device, and have functions similar to those.

Next, the detection unit 104 of the X-ray detector 111 is described.

The detection unit 104 includes a plurality of detection units arranged in an arc-like shape approximately centered around the X-ray source 100, and is configured to rotate while maintaining a positional relationship with the X-ray source 100 in conjunction with rotation of the gantry rotation unit 101. Furthermore, while, in FIG. 1, for illustrative purposes, a case where eight detection units 104 are arranged is illustrated, in the actual device, for example, about 40 detection units 104 are arranged. Moreover, an X-ray grid (not illustrated) is installed on the front surface of the detection unit 104, thus preventing X-rays scattered by, for example, the subject under test 300 out of X-rays radiated from the X-ray source 100 from falling on the detection unit 104.

The detection unit 104 has a structure in which, for example, a plurality of X-ray detection elements of the same size is two-dimensionally arranged in a channel direction and a slice direction and is arranged at regular intervals in each direction. In the X-ray CT device illustrated in FIG. 1, the X-ray detection elements are arranged with the channel direction set approximately consistent with a rotation direction 113 and with the slice direction set approximately consistent with a rotation axis direction 114.

Figure 3:
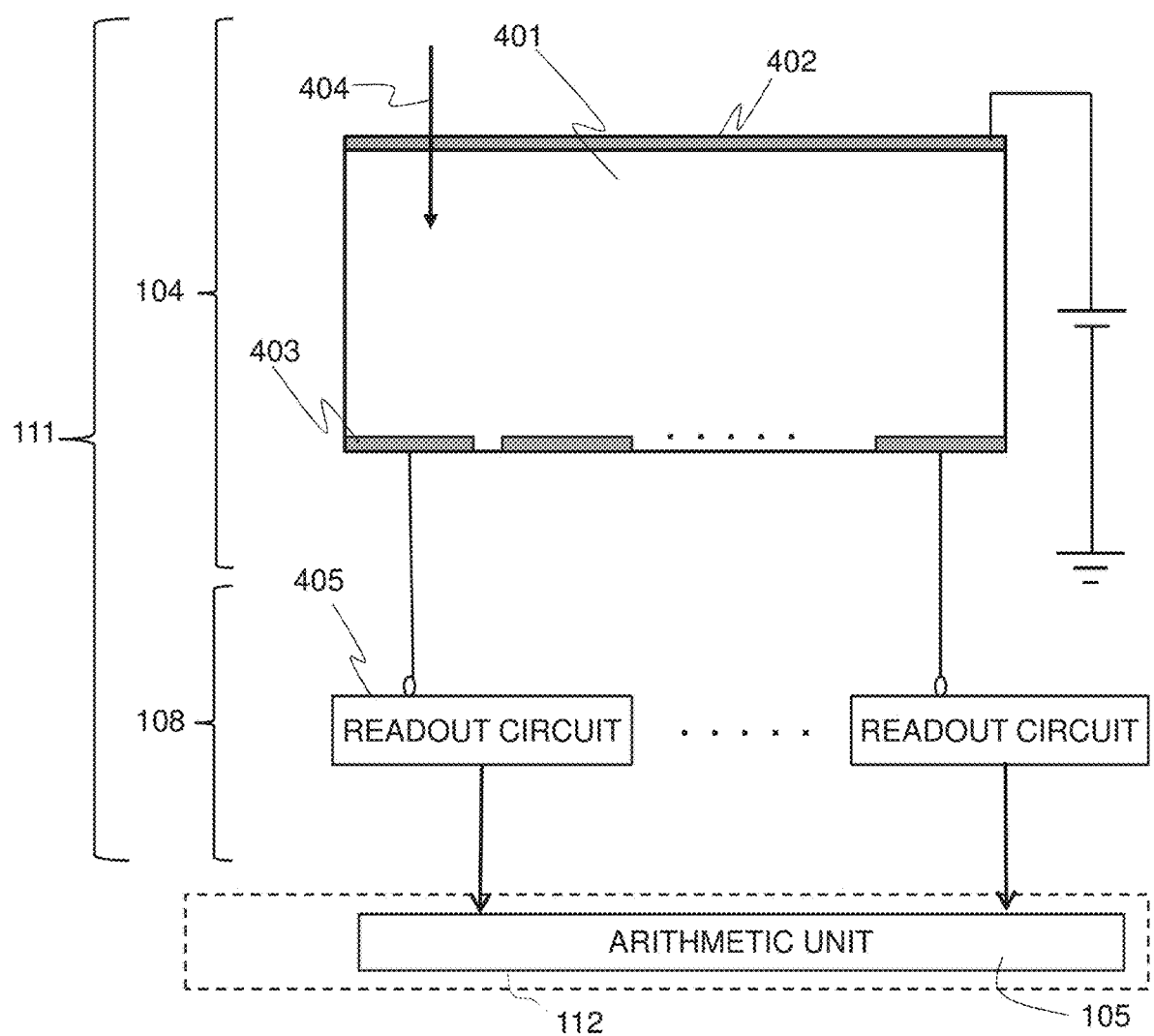
FIG. 3 is a reference diagram illustrating an outline of a detection unit in the X-ray CT device illustrated in FIG. 1.

On the other hand, the cross-section of the detection unit 104 has a structure in which, for example, as illustrated in FIG. 3, an X-ray detection element is configured with positive and negative electrodes 402 and 403 provided in such a way as to sandwich a detection layer 401, and a readout circuit 405 is connected to the electrodes 402 and 403. In the present embodiment, the positive electrode 402 has a structure in common between the X-ray detection elements.

The detection layer 401 is made from a semiconductor material, such as cadmium telluride (CdTe), cadmium zinc telluride (CdZnTe), or silicon (Si). As indicated by an arrow 404 in FIG. 2, X-rays enter the detection layer 401 from the side of the positive electrode 402, so that X-ray photons are detected and electric charges having an amount corresponding to the energy thereof are generated. Then, the detection unit 104 outputs an analog electrical signal corresponding to the electric charges to the signal collection unit 108.

The analog signal output from the detection unit 104 is input to the readout circuit 405 of the signal collection unit 108. The readout circuit 405 performs readout with incidence of X-rays as a trigger, and then performs energy discrimination and digital conversion. Energy discrimination is processing for discriminating electrical signals generated by incident electric charges between a plurality of energy ranges with use of a predetermined threshold value. At this time, since the wave height or generation amount of the generated electrical signals depends on energy of incident X-ray photons, the electrical signals are able to be discriminated between energy ranges corresponding to the X-ray photons. In this way, the electrical signals are discriminated between energy ranges and are counted individually to obtain digital signals. The signal collection unit 108 outputs the thus-obtained digital signals for the respective energy ranges to the arithmetic unit 105.

Now, an example of a discrimination method which is performed by the readout circuit 405 is described. Here, an example of discrimination into three energy ranges, i.e., an energy range which is less than a predetermined low energy threshold value (hereinafter referred to as a "low energy range"), an energy range which is greater than or equal to the predetermined low energy threshold value and is less than a predetermined high energy threshold value (hereinafter referred to as a "medium energy range"), and an energy range which is greater than or equal to the predetermined high energy threshold value (hereinafter referred to as a "high energy range") is described.

Figure 4:
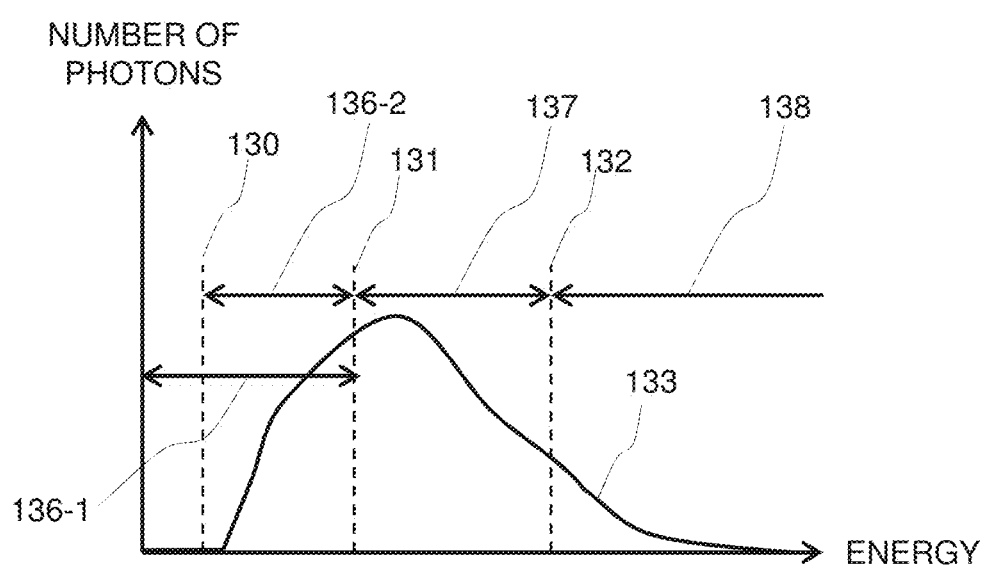
FIG. 4 is a graph illustrating a relationship between the number of photons, which are detected by the detection unit in the X-ray CT device illustrated in FIG. 1, and an energy range.

Such three energy ranges are described with reference to FIG. 4. In the graph illustrated in FIG. 4, the horizontal axis indicates energy and the vertical axis indicates the number of photons. A curved line 133 in FIG. 4 represents an example of a spectrum of X-rays falling on the X-ray detection elements of the detection unit 104. Threshold values 130 to 132 are threshold values used to determine the presence or absence of inputting of X-ray photons, and details thereof are described below. An area 136-1 is the low energy range, an area 137 is the medium energy range, and an area 138 is the high energy range. However, although details are described below, since, when the energy is at less than the threshold value 130, the readout circuit 405 does not perform readout of signal, an area 136-2 substantially serves as the low energy range. The incident X-ray photons are discriminated between energy ranges corresponding to energy by the readout circuit 405 for the respective X-ray detection elements and are then progressively counted in number for the respective energy ranges.

Figure 5:
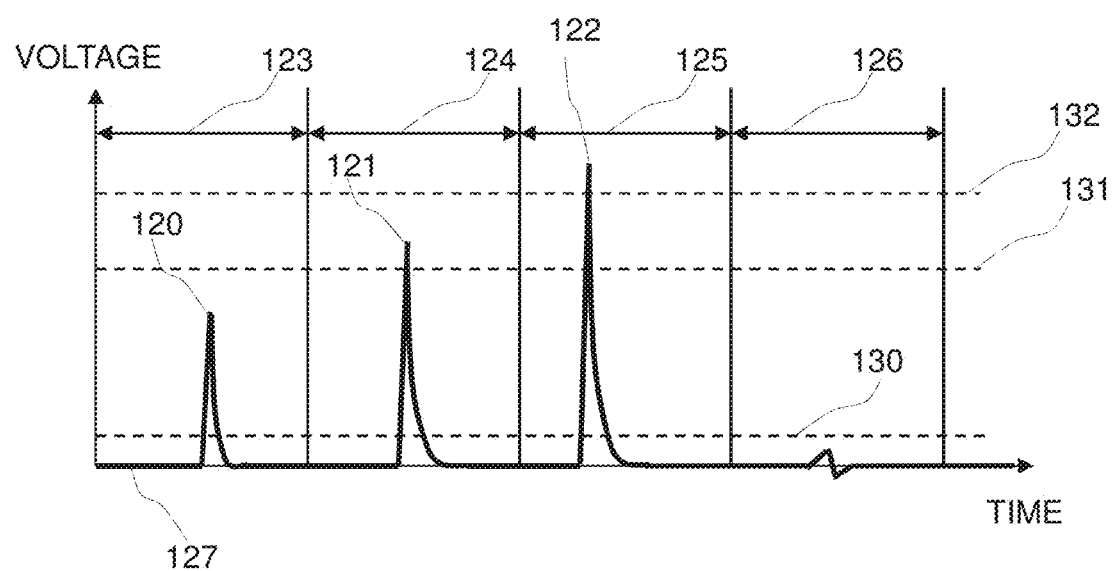
FIG. 5 is a graph illustrating a voltage signal which corresponds to electric charges generated in the detection unit in the X-ray CT device illustrated in FIG. 1.

FIG. 5 is a graph illustrating a voltage signal 127 generated by the generated electric charges, in which the horizontal axis indicates time and the vertical axis indicates voltage. Moreover, the threshold value 131 represents the low energy threshold value and the threshold value 132 represents the high energy threshold value. In the example illustrated in FIG. 5, X-rays are made incident during a sampling time 123 to generate a pulse output 120, X-rays are made incident during a sampling time 124 to generate a pulse output 121, and X-rays are made incident during a sampling time 125 to generate a pulse output 122. Furthermore, while, in FIG. 5, a case where sampling is periodically performed not only at timing when X-rays are made incident but also when X-rays are not made incident (during a sampling time 126) is illustrated, there can be a case where sampling is performed at timing when X-ray photons are made incident.

In the present embodiment, before discriminating X-ray photons caused by incident signals between energy ranges, the readout circuit 405 determines whether X-ray photons have been made incident. For that purpose, at each sampling, the readout circuit 405 compares the maximum value of the output voltage 127 in the corresponding section with the threshold value 130. Here, the threshold value 130 is a threshold value used to determine the presence or absence of inputting of X-ray photons, and, when the output voltage 120 is greater than or equal to the threshold value 130, discrimination between energy ranges described below is performed, and, when the output voltage 120 is less than the threshold value 130, it is not performed. Such a threshold value 130 is required because the voltage 127 is varying due to the circuit noise of the detection unit 104 even when X-rays are not input and, therefore, it is necessary to prevent such a variation from being erroneously detected as a signal derived from X-rays. Therefore, the threshold value 130 is set to a value larger than zero and smaller than the low energy threshold value 131.

In the sampling time 126 in FIG. 5, while X-rays are not made incident, an example in which a variation of the output voltage 127 is caused by noise is illustrated, and, since the output voltage 120 is less than the low energy threshold value 121, the readout circuit 405 does not perform discrimination between energy ranges of signals.

In a case where X-rays have been made incident and the voltage 127 which is greater than or equal to the threshold value 130 has been generated, the readout circuit 405 discriminates such signals between energy ranges and counts the number of incident X-ray photons in the respective energy ranges. This discrimination is performed by comparing the maximum value of the output voltage 127 with the low energy threshold value 131 and the high energy threshold value 132.

For example, in the sampling time 123, since the output voltage 120 is less than the low energy threshold value 131, the corresponding range is discriminated to be the low energy range. In the sampling time 124, since the output voltage 121 is greater than or equal to the low energy threshold value 131 and is less than the high energy threshold value 132, the corresponding range is discriminated to be the medium energy range. In the sampling time 125, since the output voltage 120 is greater than or equal to the high energy threshold value 132, the corresponding range is discriminated to be the high energy range.

The number of X-ray photons made incident while being discriminated between energy ranges is counted for the respective energy ranges, and the sum of the counted numbers is output for each view. The sampling time is very short in comparison with the time of a view, so that sampling is performed a large number of times between views.

In this way, discrimination of the presence or absence of incidence and discrimination between energy ranges are performed, so that the signal collection unit 108 generates a digital signal in each energy range for each view.

Furthermore, instead of performing discrimination using the maximum value at sampling, for example, performing discrimination using the integrated value of output voltages during sampling can be employed, and the method for discrimination is not limited to the above-mentioned method.

In the X-ray CT device configured in this way, usually, a photographing operation is performed as follows.

First, when a photographing operator inputs a photographing condition via the input unit 110 and inputs starting of actual photographing, the control unit 107 starts radiation of X-rays from the X-ray source 100 and controls the gantry rotation unit 101, thus starting photographing. For example, the X-ray source 100 accelerates electron beams at an X-ray tube voltage of 120 kV to radiate X-rays toward the subject under test 300 lying on the bed top plate 103. X-rays which have passed through the subject under test 300 are detected by the detection unit 104. The detection unit 104 generates electric charges corresponding to energy of incident X-rays for the respective X-ray detection elements. As mentioned above, the signal collection unit 108 discriminates these electric charges between the high energy range, the medium energy range, and the low energy range, obtains a digital signal for each energy range and for each view, and outputs the digital signal to the arithmetic unit 105.

The control unit 107 causes the gantry rotation unit 101 to rotate in the rotation direction, thus changing the angle of radiation of X-rays toward the subject under test 300. While performing rotational driving in this manner, the X-ray CT device repeatedly performs photographing with the focus position being changed for the respective views, thus acquiring digital signals for 360 degrees. Photographing is performed over a plurality of views, for example, at intervals of 0.4 degrees. With such photographing performed, digital signals for 360 degrees are obtained, and the digital signals for 360 degrees are treated as projection data. Furthermore, X-rays which are radiated from the X-ray source 100 can be pulse X-rays synchronized with the respective views or can be continuous X-rays.

The arithmetic unit 105 performs predetermined correction processing or arithmetic processing on the acquired projection data, thus generating multi-energy images. In other words, the arithmetic unit 105, which serves as an image processing unit, performs, for example, first basis material transformation, reconstructed image generation, second basis material transformation, and multi-energy image generation.

Arithmetic processing which is performed by the arithmetic unit 105 is described according to the flowchart of FIG. 6 as follows.

In the present embodiment, an example in which first basis material transformation processing is performed to calculate the physical amounts of a basis material A and a basis material B which belong to a first basis material group and second basis material transformation processing is performed to calculate the physical amounts of a basis material C and a basis material D which belong to a second basis material group different from the first basis material group is described. Moreover, an example in which surface densities are calculated as the physical amounts of the basis material A and the basis material B which belong to the first basis material group and the physical amounts of the basis material C and the basis material D which belong to the second basis material group is described.

Furthermore, the first basis material group and the second basis material group differ from each other, and there is a basis material which is included in only any one of the first basis material group and the second basis material group. On the other hand, the respective numbers of basis materials included in the first basis material group and the second basis material group can be equal to each other or can be different from each other, and, moreover, some basis materials can be included in common.

Moreover, in the following description, for ease of understanding and for descriptive purposes, signals obtained from the signal collection unit 108 are referred to as "projection data", and projection data generated by using a result of first basis material transformation or a result of second basis material transformation is referred to as a "projection image".

Figure 6:
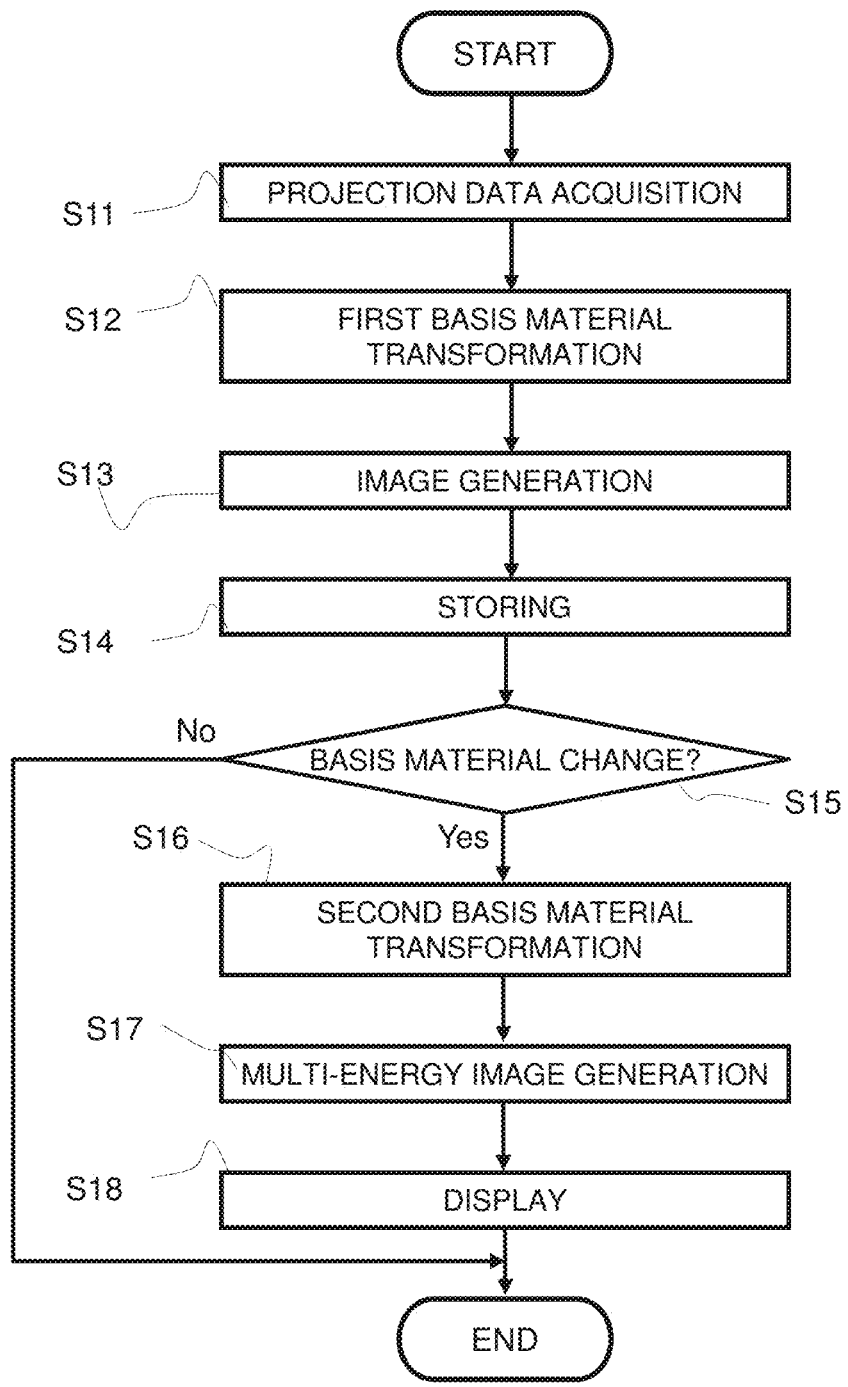
FIG. 6 is a flowchart used to explain an outline of basis material calculation processing in the X-ray CT device with the image processing device according to the embodiment of the present invention applied thereto.

As illustrated in FIG. 6, in step S11, the main control unit 159 acquires two or more types of projection data different in energy distribution. In step S12, the first basis material transformation unit 151 performs first basis material transformation based on the projection data acquired in step S11. Here, the first basis material transformation refers to calculating the physical amounts of the basis material A and the basis material B belonging to the first basis material group from two or more types of projection data different in energy distribution.

In next step S13, the projection image generation unit 152 or the reconstructed image generation unit 153 generates at least one of a projection image or a reconstructed image from the physical amounts of the basis material A and the basis material B belonging to the first basis material group calculated in step S12. In step S14, the main control unit 19 causes the storage unit 109 to store the image generated in step S13, and causes the display unit 107 to display the generated image as needed.

In next step S15, the main control unit 159 determines whether to change the basis materials subjected to calculation performed in step S12. In other words, the main control unit 159 determines whether to perform second basis material transformation. For example, in a case where the user has issued an instruction to change the basis materials, the main control unit 159 determines to perform the second basis material transformation. If it is determined to perform changing of the basis materials, the processing proceeds to step S16, in which the second basis material transformation unit 154 calculates the physical amounts of the basis material B and the basis material C belonging to the second basis material group input by the user based on the projection image or the reconstructed image generated in step S13.

In step S17, the reconstructed image generation unit 153 generates a multi-energy image using the physical amounts of the basis material B and the basis material C belonging to the second basis material group, and, in step S18, the main control unit 159 causes the display unit 107 to display the generated multi-energy image, and the processing then ends. Moreover, if, in step S15, it is determined not to change the basis materials, the processing ends.

Figure 7:
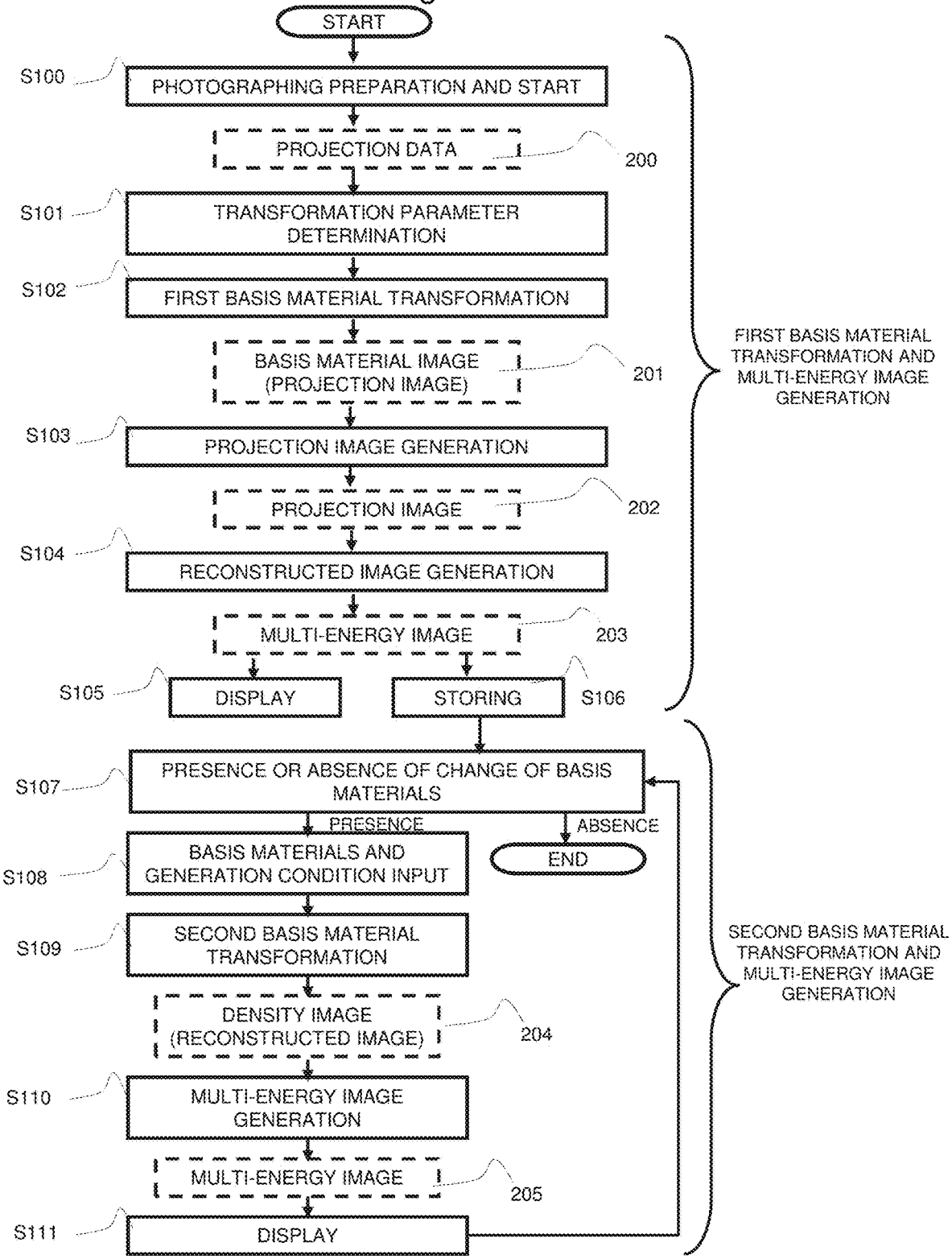
FIG. 7 is an explanatory diagram used to explain basis material calculation processing in the X-ray CT device with the image processing device according to the embodiment of the present invention applied thereto.

Details of the above-described arithmetic processing concerning basis material transformation performed by the arithmetic unit 105 and data or an image which is generated by each processing operation are described in more detail with reference to an explanatory diagram illustrated in FIG. 7. In FIG. 7, solid lines indicate contents of processing, and dashed lines indicate data or images which are generated by performing processing operations indicated by solid lines.

As illustrated in FIG. 7, processing in step S100 to step S106 is processing for calculating the physical amounts of the first basis materials and acquiring a multi-energy image, and processing in step S107 to step S110 is processing for calculating the physical amounts of the second basis materials and acquiring a new multi-energy image.

In step S100, the user performs, with respect to the X-ray CT device via the input unit 110, inputting of various settings as photographing preparations and inputting of a photographing start instruction, thus starting photographing, and the arithmetic unit 105 acquires projection data 200 from the signal collection unit 108. The photographing preparations include, for example, settings of photographing conditions, such as an X-ray tube voltage or X-ray tube current of the X-ray source 100, an X-ray irradiation range, a focus size, the type or the presence or absence of an X-ray filter, the type or the presence or absence of a bowtie filter, a photographing time, a scanning time, and a photographing range, and settings of, for example, the type of a basis material, the physical amount of a basis material, and the size or type of a reconstructed image to be generated (for example, selecting a virtual monochromatic image as a multi-energy image).

The photographing conditions as set are then stored in the storage unit 109. In the following description, a case where, as photographing condition information, an X-ray tube voltage has been stored in the storage unit 109 is particularly described.

In step S101, the transformation parameter determination unit 150 determines transformation parameters which are applied when the first basis material transformation is performed on the projection data 200 acquired from the signal collection unit 108. Here, the projection data is acquired in each of three energy ranges, i.e., a low energy range, a medium energy range, and a high energy range. The transformation parameters which are applied to basis material transformation processing are previously measured and generated prior to a main photographing operation and are then stored in the storage unit 109, and, in step S101, the transformation parameter determination unit 150 determines transformation parameters which are to be applied, from the photographing conditions stored in the storage unit 109.

As the transformation parameters which are applied to basis material transformation processing, for example, transformation maps illustrated in FIGS. 8(A) to 8(C) can be used. The transformation map illustrated in FIG. 8(A) represents output values in the low energy range which are obtained when the surface density value of the basis material A (horizontal axis) and the surface density value of the basis material B (vertical axis) have been determined, and a curved line 161 represents an example of a curved line indicating a set of combinations of the surface density value of the basis material A and the surface density value of the basis material B which a given output value can take (hereinafter referred to as a "contour line"). This means that, with respect to the same output value in the low energy range, there is a plurality of combinations of the surface density value of the basis material A and the surface density value of the basis material B.

Similarly, the transformation map illustrated in FIG. 8(B) represents output values in the medium energy range which are obtained when the surface density value of the basis material A (horizontal axis) and the surface density value of the basis material B (vertical axis) have been determined, and a curved line 155 represents an example of a contour line of a given output value. Similarly, the transformation map illustrated in FIG. 8(C) represents output values in the high energy range which are obtained when the surface density value of the basis material A (horizontal axis) and the surface density value of the basis material B (vertical axis) have been determined, and a curved line 156 represents an example of a contour line of a given output value.

Such a set of transformation maps varies depending on an X-ray irradiation situation in the respective maps. More specifically, in a case where X-ray tube voltages of 80 kVp and 120 kVp are able to be set as the photographing condition, a set of transformation maps which differ with respect to the respective X-ray tube voltages is required. Accordingly, a set of transformation maps for each photographing condition, in other words, for each X-ray tube voltage, is previously stored as transformation parameters in the storage unit 109. In step S101, the transformation parameter determination unit 150 determines one set of transformation maps based on a photographing condition, here, an X-ray tube voltage, with respect to each X-ray detection element and each view.

After the transformation parameters which are applied to the first basis material transformation processing are determined in the above-mentioned way, in next step S102, the first basis material transformation unit 151 calculates the physical amounts of the respective basis materials included in the first basis material group with use of projection data in three energy ranges, i.e., the low energy range, the medium energy range, and high energy range, and a set of transformation maps serving as the transformation parameters which are applied to the first basis material transformation processing determined in step S101, and thus generates basis material images for the first basis material group. In the present embodiment, the surface density is calculated as the physical amount. The calculation of the surface density is performed by each X-ray detection element and for each view, so that basis material images (projection images 201) composed of surface densities of the respective basis materials included in the first basis material group are acquired. Thus, as the basis material images, projection images of the respective basis materials, in the present embodiment, respective projection images 201 of the basis material A and the basis material B, are generated.

The method of determining such a surface density value is described with reference to FIG. 8(D).

FIG. 8(D) is a diagram obtained by superposing FIGS. 8(A) to 8(C), and, while data in one energy range provides a plurality of combinations of surface density values of the first basis materials, using a plurality of energy ranges causes an intersection point of data in those energy ranges to become a value satisfying results of all of the energy ranges, thus becoming an optimum surface density value of the first basis material group. In FIG. 8(D), in a case where curved lines 161, 155, and 156 are results measured in the respective energy ranges, an intersection point 157 in FIG. 8(D) becomes an optimum value, and the value on the horizontal axis of the intersection point 157 serves as the optimum surface density value of the basis material A and the value on the vertical axis of the intersection point 157 serves as the optimum surface density value of the basis material B.

However, since, due to, for example, fluctuation of the dose or quantum number of X-rays, output values of projection data have errors, a solution may not be uniquely obtained from the transformation maps. FIG. 8(E) illustrates an example of such a case where a solution is not able to be uniquely obtained. As illustrated in FIG. 8(E), an intersection point between the curved line 155 and the curved line 156 is a point 157-1, an intersection point between the curved line 161 and the curved line 155 is a point 157-2, and an intersection point between the curved line 161 and the curved line 156 is a point 157-3, so that a solution is not uniquely specified. In this case, it is necessary to estimate the most probable resolution.

In order to estimate the resolution, for example, the respective values of surface density of the basis material A and the basis material B can be changed near the intersection points 157-1, 157-2, and 157-3 by a simulation, so that a point at which artifacts become least when a reconstructed image is generated can be selected. The first basis material transformation unit 1053 can be configured to include an estimation unit (not illustrated) used to estimate such a resolution. However, since such processing requires a large calculation amount and, when being performed on projection data, would be performed for all of the X-ray detection elements and in all of the views, a lot of time may be required.

Next, in step S103, the projection image generation unit 152 generates projection images 202 of multi-energy images based on the basis material images 201. The projection images 202 include a projection image of a multi-energy image set in step S100 (hereinafter referred to as a "designated multi-energy image") and a projection image of a multi-energy image for use in the second basis material transformation (hereinafter referred to as a "multi-energy image for second basis material transformation").

Here, the multi-energy image for second basis material transformation is an image previously determined prior to photographing, and is composed of a plurality of images required for second basis material transformation. In the present embodiment, an example in which the designated multi-energy image is an image obtained at an X-ray tube voltage of 80 kVp, which is different from that used in photographing, and the multi-energy image for second basis material transformation includes virtual monochromatic images obtained at 50 keV and 100 keV is described.

Now, an example of the method of generating projection images 202 of virtual monochromatic images of the multi-energy image for second basis material transformation is described.

When monochromatic energy is denoted by $E_0$, projection images are denoted by $P_{E0}$, values of projection images of two basis materials, i.e., the basis material A and the basis material B, are denoted by δ1 and δ2, mass-absorption coefficients in energy E0 are denoted by μm1(E0) and μm2(E0), and the number of photons in energy E0 is denoted by S(E0), projection images PE0 are able to be calculated by using, for example, formula (1) with use of values δ1 and δ2 of surface density projection images of two basis materials calculated by the first basis material transformation unit 151.

[Math. 1]

$$P_{E0} = S(E_0) \cdot \exp[-\mu m_1(E_0)\delta_1 - \mu m_2(E_0)\delta_2] \quad (1)$$

Employing the case of 50 keV and the case of 100 keV for energy $E_0$ enables generating projection images 202 of the respective virtual monochromatic images.

Next, an example of the method of generating an image obtained at an X-ray tube voltage of 80 kVp as the designated multi-energy image is described.

In the case of an X-ray tube voltage of 80 kVp, the number of photons of an X-ray spectrum which is radiated at the time of the X-ray tube voltage being 80 kVp is used as the number of photons $S(E_0)$, virtual monochromatic images are obtained when energy $E_0$ in formula (1) is 0 keV to 80 keV, and the obtained virtual monochromatic images are integrated, so that a projection image of the virtual monochromatic image can be obtained. Here, for example, virtual monochromatic images are obtained in increments of 1 keV and the obtained virtual monochromatic images are added together as in formula (2), so that a projection image $P_{80kVp}$ obtained at an X-ray tube voltage of 80 kVp can be generated.

[Math. 2]

$$P_{80kVp} = \int_{0keV}^{80keV} P_{E0} dE_0 = \sum_{E_0=0keV}^{80keV} S(E_0) \cdot \exp[-\mu m_1(E_0)\delta_1 - \mu m_2(E_0)\delta_2] \quad (2)$$

Various images can be generated as the designated multi-energy image, such as reconstructed images indicating a distribution of other than absorption coefficients, including, for example, a virtual monochromatic image, a basis material density image, an effective atomic number image, an electron density image, a photoelectric effect image, and a Compton scattering image.

Moreover, while, in the present embodiment, virtual monochromatic images obtained at 50 keV and 100 keV have been described as the multi-energy image for second basis material transformation, the combination of X-ray tube voltages is not limited to this, but combinations of virtual monochromatic images in various types of energy can be applied. Not only a combination of two types of energy but also a combination of three or more types of energy can also be used. Additionally, images obtained at a plurality of different X-ray tube voltages can be used. Moreover, reconstructed images in the respective energy ranges, in other words, a set of reconstructed images corresponding to some or all of the energy ranges including the low energy range, the medium energy range, and the high energy range can be used. Additionally, a set of various multi-energy images, such as an effective atomic number image, an electron density image, a photoelectric effect image, and a Compton scattering image can be used.

Next, in step S104, the reconstructed image generation unit 153 performs reconstruction processing on the projection images 202 obtained in step S103, thus generating reconstructed images. The reconstructed image generation unit 153 first reconstructs a projection image of the designated multi-energy image to generate a designated multi-energy image, and displays the designated multi-energy image in step S105. Next, the reconstructed image generation unit 153 reconstructs a projection image of the multi-energy image for second basis material transformation to generate a multi-energy image for second basis material transformation, and stores the generated multi-energy image for second basis material transformation in the storage unit 109 in step S106.

For reconstruction processing, for example, various techniques such as a Feldkamp image reconstruction method can be applied.

Furthermore, in step S105, the arithmetic unit 105 is able to display only the designated multi-energy image on the display unit 107, and is further able to display the multi-energy image for second basis material transformation together with the designated multi-energy image. Moreover, in step S106, the arithmetic unit 105 is also able to store the designated multi-energy image in addition to the multi-energy image for second basis material transformation.

Next, in step S107, the second basis material transformation unit 154 receives, via the input unit 110, inputting of the presence or absence of change of basis materials performed by the user. When the second basis material transformation unit 154 receives an input indicating not to change the basis materials from the user, the processing ends. On the other hand, when the second basis material transformation unit 154 receives an input indicating to change the basis materials, the processing proceeds to next step S108.

In step S108, the second basis material transformation unit 154 receives, via the input unit 110, inputting of a basis material which is to be calculated and a generation condition. Here, the basis material input by the user via the input unit 110 is a basis material included in the second basis material group (assumed to be the basis material C and the basis material D), and is different from the basis material A and the basis material B included in the first basis material group. Moreover, the generation condition includes, for example, the size and type of a multi-energy image to be generated.

When inputting of basis materials and a generation condition in step S108 is completed, the processing then proceeds to step S109, in which the second basis material transformation unit 154 reads out the multi-energy image for second basis material transformation stored in the storage unit 109, and calculates the physical amounts of the second basis materials.

An example of the method of calculating the physical amounts of the basis material C and the basis material D included in the second basis material group is described as follows with reference to FIG. 9. In the present embodiment, an example of the method of calculating the densities of the basis material C and the basis material D included in the second basis material group and generating virtual monochromatic images obtained at energy 50 keV and energy 100 keV as the multi-energy image for second basis material transformation is described.

To calculate the densities of the basis material C and the basis material D, for example, transformation maps are used similarly to the case of being used to calculate the surface densities of the first basis materials. The transformation maps are previously stored in the storage unit 109 for the respective multi-energy images for second basis material transformation. In the case of the present embodiment, the transformation map illustrated in FIG. 9(A) is used for a virtual monochromatic image at energy 50 keV, and the transformation map illustrated in FIG. 9(B) is used for a virtual monochromatic image at energy 100 keV. In FIG. 9(A), the horizontal axis indicates the density value of the basis material C and the vertical axis indicates the density value of the basis material D. Since, with respect to the multi-energy image for second basis material transformation, a spectrum of incident X-rays supposed to be 50 keV is previously determined, mass-absorption coefficients of the basis material C and the basis material D are obtained, so that, each time a combination of the density value of the basis material C and the density value of the basis material D is determined, pixel values of the reconstructed image (hereinafter, each pixel of the reconstructed image being referred to as a "voxel" and its pixel value being referred to as a "voxel value") are obtained. In FIGS. 9(A) and 9(C), a curved line 158 is a curved line representing a set of combinations of the density value of the basis material C and the density value of the basis material D which a given voxel value is able to take (hereinafter referred to as a "contour line").

In the transformation map for a virtual monochromatic image at energy 100 keV illustrated in FIG. 9(B), a curved line 159 is a curved line (contour line) representing combinations of the density value of the basis material C and the density value of the basis material D which a given voxel value is able to take. FIG. 9(C) is a diagram obtained by superposing FIG. 9(A) and FIG. 9(B), and an intersection point 160 between the curved line 158 and the curved line 159 serves as optimum density values of the basis material C and the basis material D.

Figure 8:
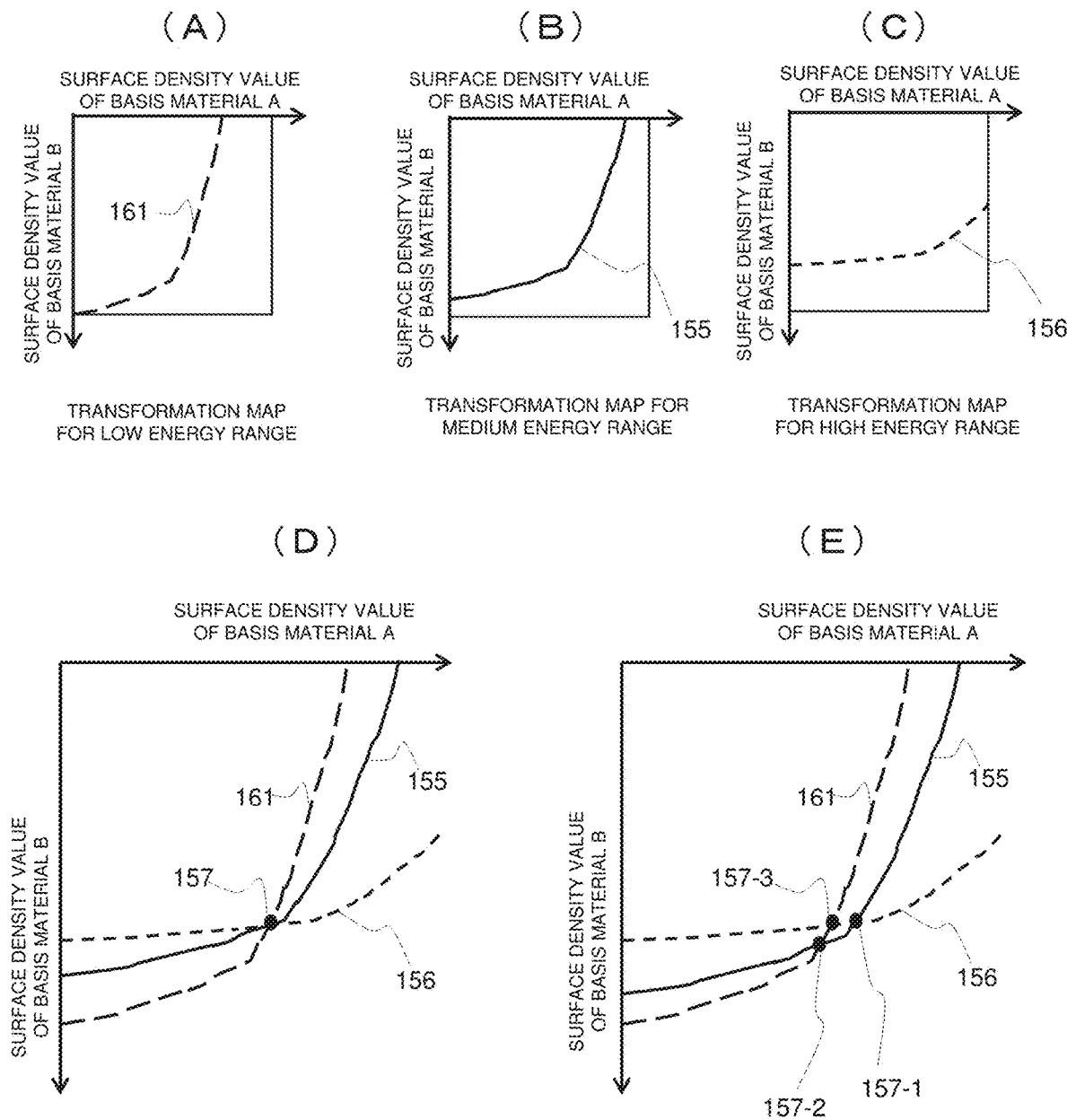
FIGS. 8(A) to 8(E) are examples of transformation maps which are used in the basis material calculation processing in the X-ray CT device with the image processing device according to the embodiment of the present invention applied thereto.

While, in the above-mentioned example, an example of performing the second basis material transformation using two reconstructed images of energy 50 keV and energy 100 keV has been described, using three or more reconstructed images can also be employed. At this time, in a case where, as illustrated in FIG. 8, a resolution is not able to be uniquely obtained, for example, it is favorable to estimate a resolution by a simulation. Since the number of voxels of a reconstructed image is smaller than that of projection data, processing can be performed in a shorter time as compared with the case of performing estimation from projection data.

In step S109, the above-described processing is performed with respect to all of the voxels of the reconstructed image to generate a density image 204, which is a set of density values. The density image 204 is generated with respect to both the basis material C and the basis material D.

In next step S110, the reconstructed image generation unit 153 generates a multi-energy image from the density image 204. An example in which a virtual monochromatic image is generated as an example of the multi-energy image is described as follows.

Absorption coefficients (linear attenuation coefficients) μ(E) in energy E are calculated with respect to all of the voxels of the reconstructed image. The absorption coefficients μ(E) are calculated according to the following formula (3).

[Math. 3]

$$M(E) = c_3\, \mu m_3(E) + c_4\, \mu m_4(E) \qquad (3)$$

In this respect, μmn(E) denotes the mass absorption coefficient of the basis material, and cn denotes the density of the basis material. The density cn of the basis material becomes the value of the density image 204, and, for example, a literature value is used as the mass absorption coefficient μmn(E). Moreover, n denotes the type of the basis material, and, when the type is the basis material C, n=3 is set and, when the type is the basis material D, n=4 is set.

The absorption coefficients are obtained with respect to all of the voxels of the reconstructed image in the above-described way and are then converted into CT values, so that a virtual monochromatic image can be generated as a multi-energy image (reconstructed image) 205. In next step S111, the arithmetic unit 105 causes the generated multi-energy image 205 to be displayed.

After this, the processing returns to step S107, in which the second basis material transformation unit 154 receives, via the input unit 110, inputting of the presence or absence of change of basis materials performed by the user. When the second basis material transformation unit 154 receives an input indicating not to change the basis materials from the user, the processing ends. On the other hand, when the second basis material transformation unit 154 receives an input indicating to change the basis materials, the arithmetic unit 105 repeats processing operations in step S108 and subsequent steps, thus generating a multi-energy image 205 again and then causing the generated multi-energy image 205 to be displayed. Performing such processing enables changing the second basis materials and repeatedly acquiring a multi-energy image for every second basis materials.

According to the present embodiment, in performing first basis material transformation, transformation parameters corresponding to X-ray irradiation conditions which combinations of basis materials included in the first basis material group can take are previously stored in the storage unit 109, so that the physical amounts of the basis materials can be calculated.

Then, in second basis material transformation, since projection data or a reconstructed image as previously obtained is used to perform transformation with respect to basis materials included in the second basis material group, in other words, to calculate the physical amounts of the basis materials, the projection data and the reconstructed data do not depend on the X-ray irradiation conditions, and basis material transformation processing can be performed only by storing transformation parameters corresponding to one X-ray irradiation condition in the storage unit 109.

More specifically, in the case of obtaining a previously determined physical amount by performing basis material transformation once, transformation parameters corresponding to possible combinations of basis materials included as a basis material group are required as much as the number of transformation parameters corresponding to possible X-ray irradiation conditions, so that a huge number of transformation parameters are required. On the other hand, according to the above-described embodiment, not only the man-hour for previously preparing transformation parameters used to transform basis materials can be reduced, but also it is not necessary to store a huge number of transformation parameters.

Moreover, it is not necessary to photograph an object each time transformation processing of a basis material is performed, so that calculation cost in the arithmetic unit 105 can be reduced.

Additionally, while some processing time may be required to calculate the physical amount of a basis material from projection data, in the case of calculating the physical amount of a basis material from a reconstructed image, since the number of voxels of the reconstructed image is smaller than that of projection data, processing can be performed at high speed.

In this way, according to the present embodiment, even in the case of switching from the first basis material group initially subjected to calculation and then calculating the physical amounts of basis materials included in the second basis material group, it is not necessary to re-perform photographing or perform a large number of arithmetic processing operations from projection data, and it is possible to acquire a multi-energy image indicating the physical amount of a desired basis material in a short time.

Furthermore, while, in the above-described embodiment, an example in which, irrespective of whether to change basis materials (whether to perform second basis material transformation), a multi-energy image for use in second basis material transformation is generated has been described, timing for generation of the multi-energy image for use in second basis material transformation can be determined as appropriate. For example, after inputting of an instruction for changing the basis materials, a multi-energy image for second basis material transformation can be generated, second basis material transformation processing and generation of a multi-energy image can be performed with use of the multi-energy image for second basis material transformation, and a multi-energy image of the changed basis materials can be generated.

(Example of User Interface in Display Unit 106)

An example of a user interface screen which is displayed on the display unit 106 of the X-ray CT device according to the above-described embodiment is described as follows.

Figure 10:
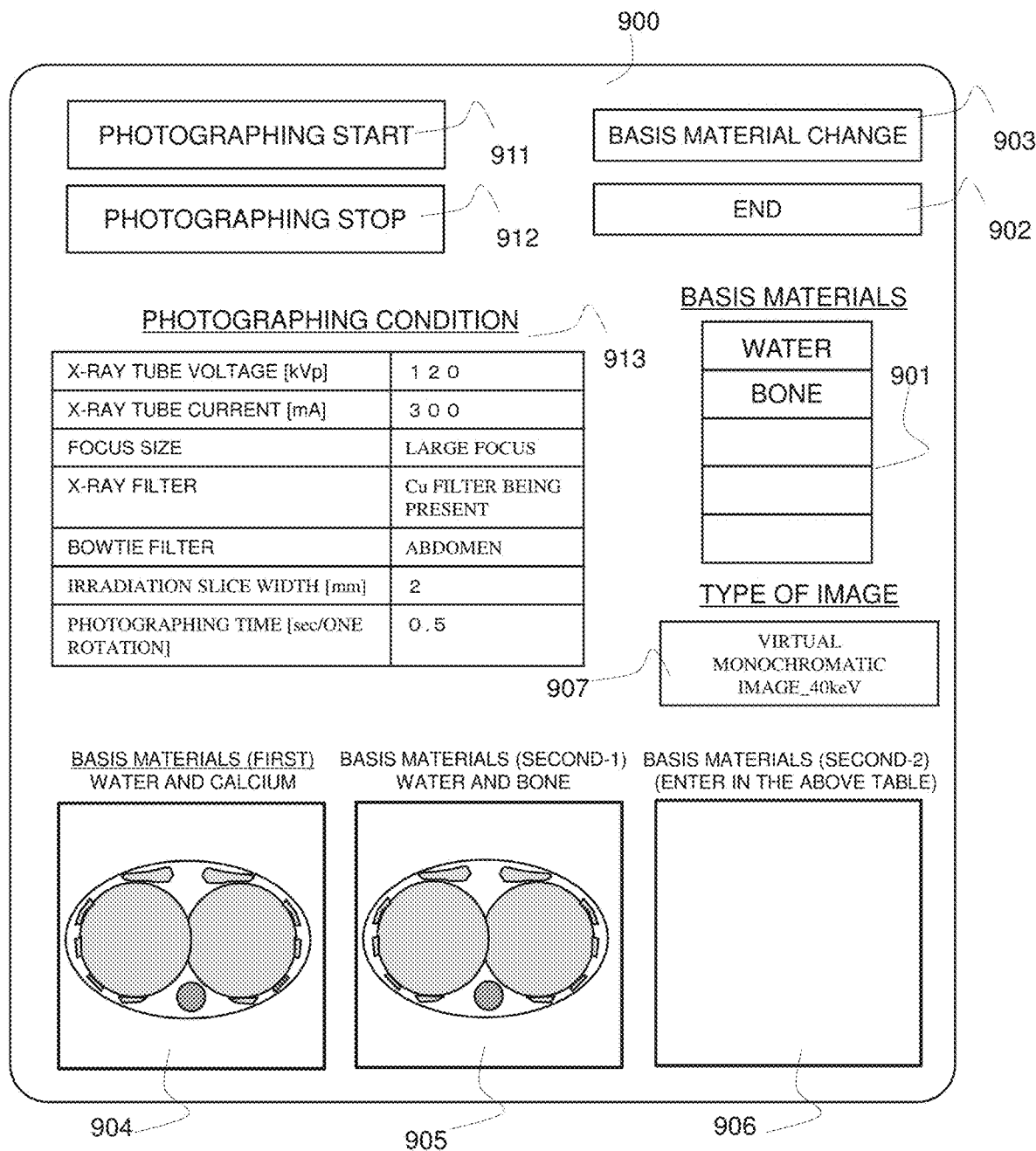
FIG. 10 is a reference diagram illustrating an example of a user interface screen which is displayed on a display unit in the X-ray CT device with the image processing device according to the embodiment of the present invention applied thereto.

FIG. 10 illustrates an example of a user interface screen which is displayed on the display unit 106. The user interface screen 900 illustrated in FIG. 10 includes a photographing start input button 911, a photographing stop button 912, a photographing condition setting region 913, a basis material setting region 901, an image type input button 907, a basis material change button 903, an end button 902, and image display regions 904, 905, and 906.

The photographing condition setting region 913 is a region used to set and input a photographing condition prior to photographing. In the example illustrated in FIG. 10, an X-ray tube voltage, an X-ray tube current, an X-ray irradiation range (irradiation slice width), a focus size, an X-ray filter (type and presence or absence), a bowtie filter (type and presence or absence), and a photographing time are displayed as an X-ray irradiation condition.

The photographing start input button 911 receives a photographing start instruction in response to being pressed by the user. In the case of stopping photographing after starting photographing, the photographing stop input button 912 receives a photographing stop instruction in response to being pressed.

With regard to the image display regions 904, 905, and 906, for example, a multi-energy image generated from the first basis materials is displayed in the image display regions 904, and a multi-energy image generated from the first basis materials is displayed in the image display regions 905.

The basis material change button 903 receives an input indicating whether to change basis materials. When the basis material change button 903 is pressed by the user, the user is then allowed to set the second basis materials in the basis material setting region 901 and to set the type of a multi-energy image via the image type input button 907. The example illustrated in FIG. 10 represents an example in which the user has selected a virtual monochromatic image of 40 keV as the type of a multi-energy image. In the basis material setting region 901, two or more sets of combined basis materials are able to be set, and the user is allowed to set one of the two or more sets. The example illustrated in FIG. 10 represents an example in which water and bone have been selected as basis materials.

When not intending to change the basis materials, the user presses the end button 902.

Next, when an instruction to start processing is issued via the basis material change button 903 for basis material transformation, a multi-energy image obtained by calculating the second basis materials which have been changed by setting is generated by the arithmetic unit 105, and is then displayed in the image display region 906.

In the case of iteratively changing the second basis materials and then generating a multi-energy image, iteratively performing the above-mentioned setting and inputting enables images to be generated and displayed any number of times.

The generated images are displayed in the image display regions 904, 905, and 906, and can be further displayed in any other image display regions additionally provided. There is an advantage in that the user can perform inputting while conforming information required for photographing or transformation of basis materials and, when simultaneously displaying, in a single screen, images which differ from each other in the types or the number of basis materials, the user can compare a plurality of images with each other and easily recognize a difference between the displayed images.

While, in the above-mentioned example, a case where the first basis material group includes one set composed of two basis materials (water and calcium) and the second basis material group includes one set composed of two basis materials (water and bone) has been described, a combination of basis materials included in each basis material group can be changed as appropriate. However, if the number of basis materials included in the first basis material group is large, the number of parameters for transformation which become needed in conjunction with such basis materials increases, and, therefore, it is favorable that the number of basis materials included in the first basis material group is smaller than the number of basis materials included in the second basis material group.

While, in the above-mentioned example, an example in which a multi-energy image for second basis material transformation is stored has been described, the present embodiment is not limited to this, but, for example, a projection image of a multi-energy image for basis material transformation can be stored. Specifically, a projection image 202 of a multi-energy image for second basis material transformation can be kept stored, inputting of the presence or absence of change of basis materials S107 can be waited while the reconstructed image generation S104 is not performed, and, only when "presence" is selected in the presence or absence of change of basis materials S107, a multi-energy image for second basis material transformation 203 can be generated by performing a reconstruction calculation 203 on that projection image, so that processing operations in the presence or absence of change of basis materials S107 and subsequent steps can be performed with use of that image.

However, generation and displaying of the designated multi-energy image S105 are caused to be completed before the presence or absence of change of basis materials S107, as with the procedure illustrated in FIG. 7. This enables reducing a time required until the processing shifts to the presence or absence of change of basis materials S107 and, particularly, reducing the processing time taken in a case where "absence" is selected in the presence or absence of change of basis materials S107.

Similarly, for example, a basis material image 201 can be kept stored, inputting of the presence or absence of change of basis materials S107 can be waited while the projection image generation S103 and the reconstructed image generation S104 are not performed, and, only when "presence" is selected in the presence or absence of change of basis materials S107, a multi-energy image for second basis material transformation 203 can be generated by performing a projection image generation S103 and a reconstruction calculation 203 on that basis material image 201, so that processing operations in the presence or absence of change of basis materials S107 and subsequent steps can be performed with use of that image.

However, generation and displaying of the designated multi-energy image S105 are caused to be completed before the presence or absence of change of basis materials S107, as with the procedure illustrated in FIG. 7. This similarly enables reducing a time required until the processing shifts to the presence or absence of change of basis materials S107.

Modification Example 1

While, in the arithmetic processing performed by the arithmetic unit 105 described in FIG. 7, an example in which the second basis material transformation unit 1058 performs the second basis material transformation processing based on the reconstructed image has been described, the second basis material transformation processing can be performed for second basis material transformation with use of the basis material image 201, which is a projection image of basis materials included in the first basis material group or the projection image 202 of a multi-energy image generated from the basis material image.

In this case, after the second basis material transformation is performed, a projection image of the physical amounts of basis materials included in the second basis material group can be obtained, and a projection image of a multi-energy image can be generated from the projection image of basis materials, and, furthermore, a multi-energy image can be acquired by performing reconstruction processing on the projection image of a multi-energy image.

Figure 11:
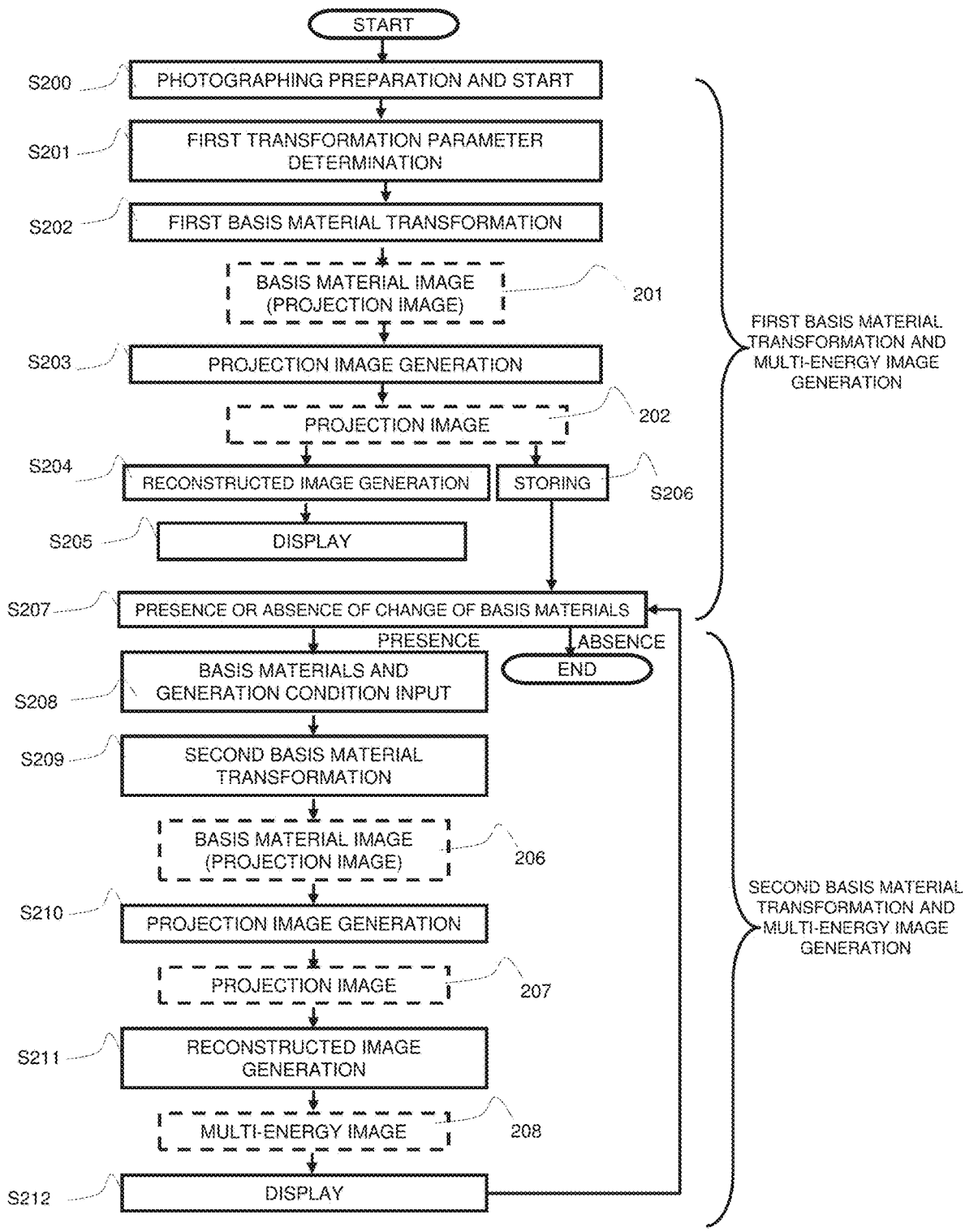
FIG. 11 is an explanatory diagram used to explain basis material calculation processing in an X-ray CT device with an image processing device according to a modification example 1 of the embodiment of the present invention applied thereto.

Details of arithmetic processing which is performed for basis material transformation by the arithmetic unit 105 in the above case and examples of data or images which are generated in that processing are described according to FIG. 11. In FIG. 11, solid lines indicate contents of processing, and dashed lines indicate data or images which are generated by performing processing operations indicated by solid lines.

As illustrated in FIG. 11, in step S200, the user performs, with respect to the X-ray CT device via the input unit 110, inputting of various settings as photographing preparations and inputting of a photographing start instruction, thus starting photographing. In next step S201, the arithmetic unit 105 determines transformation parameters, and, in step S202, the arithmetic unit 105 performs first basis material transformation, thus generating a basis material image (projection image) 201. Then, in step S203, the projection image generation unit 1055 generates a projection image 202 of a multi-energy image based on projection images for the respective basis materials. The projection image generated at this time includes a projection image for the designated multi-energy image and a projection image for the multi-energy image for second basis material transformation.

In step S204, the reconstructed image generation unit 153 performs reconstruction processing on a projection image for the designated multi-energy image generated in step S203, thus generating a multi-energy image, and, in next step S205, the arithmetic unit 105 causes the display unit 106 to display the generated multi-energy image. On the other hand, the projection image generation unit 151 stores the generated projection image of the multi-energy image for second basis material transformation in the storage unit 109 (step S206).

Next, in step S207, the second basis material transformation unit 154 receives, via the input unit 110, inputting of the presence or absence of change of basis materials performed by the user. When the second basis material transformation unit 154 receives an input indicating not to change the basis materials from the user, the processing ends. On the other hand, when the second basis material transformation unit 154 receives an input indicating to change the basis materials, the processing proceeds to next step S208.

In step S208, the second basis material transformation unit 154 receives, via the input unit 110, inputting of a basis material which is to be calculated and a generation condition for a basis material image. In next step S209, the second basis material transformation unit 154 performs second basis material transformation based on the input information, thus generating a basis material image (projection image) 206. The second basis material transformation unit 154 performs the second basis material transformation in step S209 with use of the projection image for the multi-energy image for second basis material transformation stored in the storage unit 109. This can be performed by applying, for example, the above-mentioned transformation map.

Next, in step S210, the reconstructed image generation unit 153 generates a projection image 207 of a multi-energy image with use of the basis material image (projection image) 206, then, in next step S211, the reconstructed image generation unit 153 performs reconstruction processing, thus generating a multi-energy image 208, and, in step S212, the main control unit 159 causes the display unit 106 to display the multi-energy image 208. Then, the processing returns to step S107, in which the arithmetic unit 105 receives inputting of the presence or absence of change of basis materials again.

When the second basis material transformation unit 154 receives an input indicating not to change the basis materials from the user, the processing ends. On the other hand, when the second basis material transformation unit 154 receives an input indicating to change the basis materials, the arithmetic unit 105 repeats processing operations in step S208 and subsequent steps, thus generating a multi-energy image 208 again and displaying the multi-energy image 208. Such processing enables changing the second basis materials and iteratively acquiring multi-energy images for the respective second basis materials.

Modification Example 2

In the above-described embodiment, an example in which the second basis material transformation processing is performed based on the reconstructed image has been described, and, in the modification example 1, an example in which the second basis material transformation is performed based on the projection image 202 of a multi-energy image has been described. In the following, an example in which the second basis material transformation is performed based on the basis material image 201, which is a projection image of basis materials included in the first basis material group, is described according to FIG. 12.

Figure 12:
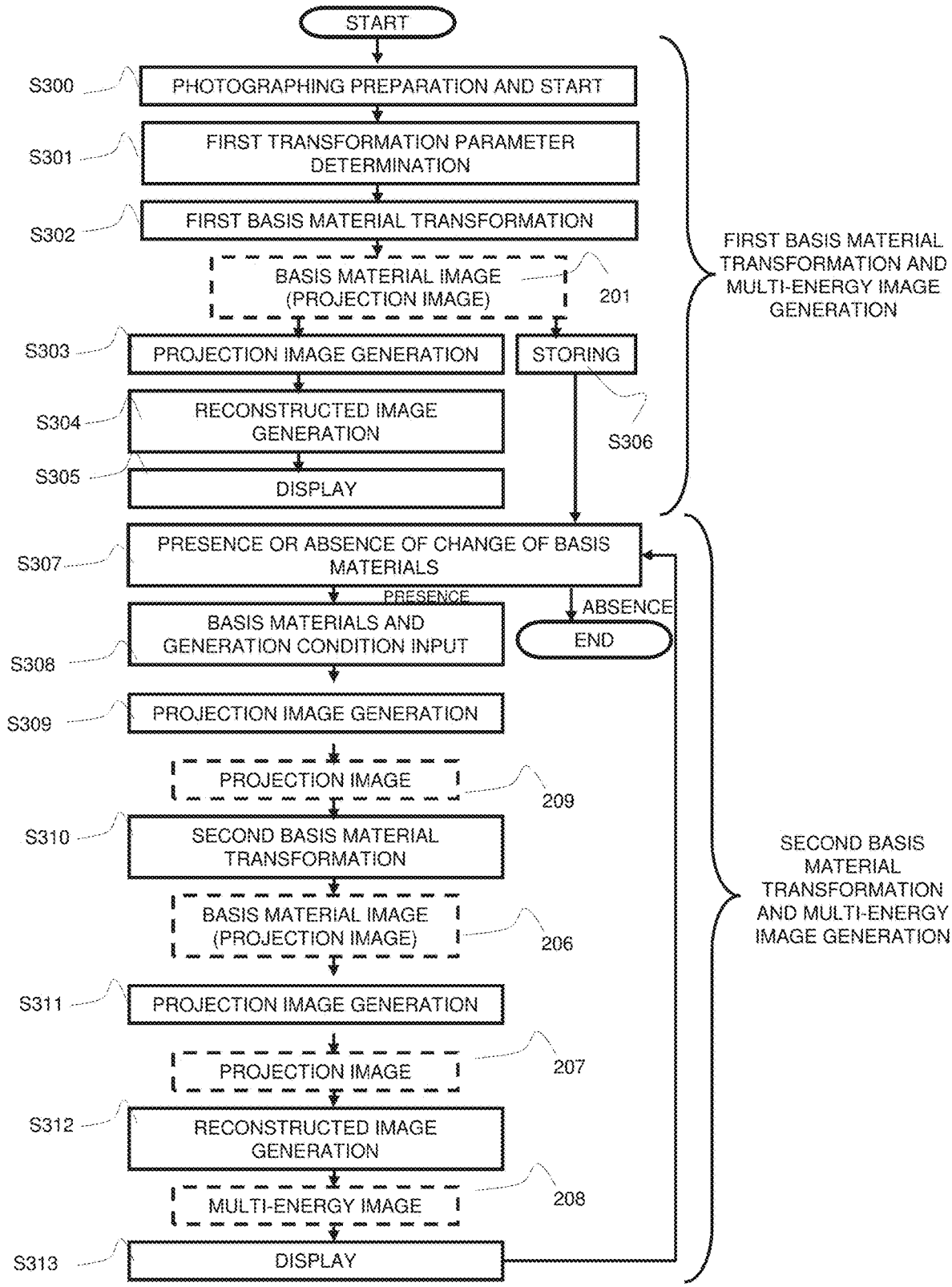
FIG. 12 is an explanatory diagram used to explain basis material calculation processing in an X-ray CT device with an image processing device according to a modification example 2 of the embodiment of the present invention applied thereto.

As illustrated in FIG. 12, in step S300, the user performs, with respect to the X-ray CT device via the input unit 110, inputting of various settings as photographing preparations and inputting of a photographing start instruction, thus starting photographing. In next step S301, the arithmetic unit 105 determines transformation parameters, and, in step S302, the arithmetic unit 105 performs first basis material transformation, thus generating a basis material image (projection image) 201.

Then, in step S303, the projection image generation unit 152 generates a projection image 202 of a multi-energy image based on projection images for the respective basis materials. The projection image generated at this time includes a projection image for the designated multi-energy image.

In step S304, the reconstructed image generation unit 153 performs reconstruction processing on the projection image for the designated multi-energy image generated in step S203, thus generating a multi-energy image, and, in next step S305, the arithmetic unit 105 causes the display unit 106 to display the generated multi-energy image.

In step S307, the arithmetic unit 105 receives inputting of the presence or absence of change of basis materials, and, when the arithmetic unit 105 receives an input indicating not to change the basis materials, the processing ends. On the other hand, when the arithmetic unit 105 receives an input indicating to change the basis materials, then in next step S308, the arithmetic unit 105 receives inputting of a basis material and a generation condition. In step S309, the arithmetic unit 105 generates a projection image of the multi-energy image for second basis material transformation based on such received information.

Performing processing operations in step S310 to step S313 with use of the projection image 209 of the multi-energy image for second basis material transformation enables generating and displaying a multi-energy image 208. Then, the processing returns to step S107, in which the arithmetic unit 105 receives inputting of the presence or absence of change of basis materials again.

In this way, before the multi-energy image for second basis material transformation or a projection image thereof is generated, a multi-energy image obtained after first basis material transformation is able to be displayed, and, therefore, an image which is intended to be referred to is able to be displayed more promptly.

In the above-described arithmetic processing which is performed by the arithmetic unit 105, for example, correction processing for sensitivity characteristics of an X-ray detection element or correction processing for estimating an output value of a defective element can be added as appropriate. Such processing enables implementing, for example, a reduction in artifact or an improvement in quantitative capability of a CT value, so that a more high-quality image can be obtained.

Moreover, for example, in a case where only one X-ray irradiation condition is available for photographing, transformation parameters are uniquely determined, so that processing for determining transformation parameters becomes unnecessary.

Moreover, while, in the above-described embodiment and modification examples thereof, an example in which an X-ray tube voltage is stored and used as a photographing condition has been described, for example, one or some of, for example, an X-ray tube current, an X-ray irradiation range (for example, a channel direction or slice direction), a focus size, the type and presence or absence of an X-ray filter or a bowtie filter, and a photographing time can be used.

while, in the above-described embodiment and modification examples thereof, an example in which, as the flow of processing which is performed by the arithmetic unit 105, after a multi-energy image of basis materials is displayed, information about the second basis materials is input has been described, for example, information about the second basis materials or the presence of absence of generation of the multi-energy image of the second basis materials can be input prior to photographing. Moreover, after a multi-energy image generated from the first basis materials is displayed, a multi-energy image of the second basis materials can be automatically generated and displayed.

In the above description, the physical amount of the first basis material is assumed to be a surface density and the physical amount of the second basis material is assumed to be a density, but both of the physical amounts can be assumed to be a physical amount which does not depend on other types of energy. For example, the physical amount of the first basis material can be assumed to be the length of a basis material, and, additionally, in a case where the second basis material transformation is performed with a reconstructed image, the physical amount of the second basis material can also be assumed to be, besides a density, the abundance ratio of a basis material. Moreover, in a case where the second basis material transformation is performed with a projection image, the physical amount of the second basis material can also be assumed to be a surface density or the length of a basis material.

The energy ranges are also not limited to the above-mentioned example, but can be set as two energy ranges, or can also be set as four or more energy ranges.

While, in the above-described embodiment and modification examples thereof, an X-ray CT device equipped with a detector of the photon counting system, which performs counting while X-rays are discriminated into two or more energy ranges, has been described, the X-ray CT device can be a dual-energy X-ray CT device or a multi-energy X-ray CT device, which is equipped with an X-ray detector of the integration type that integrates and outputs energy of a plurality of X-ray photons and which obtains a reconstructed image from a plurality of pieces of projection data obtained by photographing an object with two or more different X-ray energy distributions.

At this time, the method of obtaining projection data with two or more different X-ray energy distributions can include a method which, inside the X-ray detector, separates X-rays into two or more different energy distributions and detects X-rays with respect to the respective distributions and a method which radiates X-rays of two or more spectra from an X-ray source and obtains projection data with respect to the respective spectra. The method of radiating X-rays can include a method of switching spectra of irradiation X-rays for every half rotation, every rotation, or every plurality of rotations and a method of switching spectra of irradiation X-rays for every view or every plurality of views. Moreover, different energy distributions can be radiated in the slice direction to perform helical photographing, so that pieces of projection data with different energy distributions can be obtained with the same path.

Furthermore, while, in the above-described embodiment and modification examples thereof, an example in which projection data is acquired by an X-ray CT device performing image capturing and arithmetic processing is performed on the acquired projection data has been described, a configuration in which projection data is acquired from another photographing device and arithmetic processing is performed on such acquired projection data can be employed. Thus, an image processing device which acquires projection data obtained by a separate X-ray imaging device performing image capturing and then performs arithmetic processing on the acquired projection data can be configured.

Figure 13:
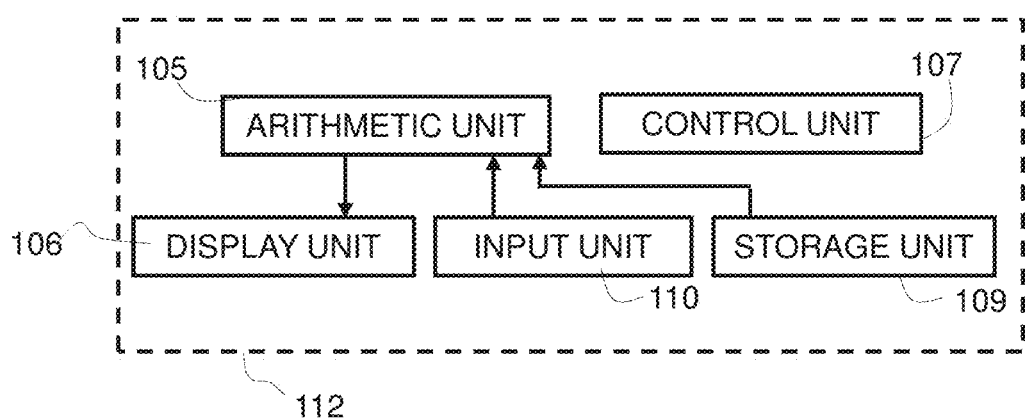
FIG. 13 is a block diagram of an image processing device according to the present invention.

Specifically, as illustrated in FIG. 13, an image processing device which includes an arithmetic unit 105, a display unit 106, control unit 107, a storage unit 109, and an input unit 110 can be configured. The image processing device illustrated in FIG. 13, for example, causes the input unit 110 to input projection data obtained by a separate X-ray imaging device performing photographing, causes the storage unit 109 to store the input projection data, and causes the arithmetic unit 105 to generate desired images, such as projection data, a projection image, and a multi-energy image, based on the stored projection data.

The above-described embodiment and modification examples thereof have been described with regard to an X-ray CT device, but can also be applied to, for example, a device which does not involve image reconstruction processing or a device which is not equipped with an X-ray source. Specifically, those can also be applied to, for example, an X-ray diagnostic imaging device, an X-ray image photographing device, an X-ray image fluoroscopic device, a mammography device, a digital subtraction device, an X-ray detector, and a radiation detector.

DESCRIPTION OF REFERENCE NUMERALS AND SIGNS

104 . . . detection unit, 105 . . . arithmetic unit, 106 . . . display unit, 107 . . . control unit, 108 . . . signal collection unit, 109 . . . storage unit, 110 . . . input unit, 111 . . . X-ray detector, 112 signal processing unit, 140 photographing condition information, 141 . . . transformation parameters, 150 . . . transformation parameter determination unit, 151 . . . first basis material transformation unit, 152 . . . projection image generation unit, 153 . . . reconstructed image generation unit, 154 . . . second basis material transformation unit, and 159 . . . main control unit.

The invention claimed is:

1. An image processing device comprising:
a first basis material transformation unit that calculates each of physical amounts of two or more basis materials included in a first basis material group based on two or more types of projection data different in energy distribution;
an image generation unit that generates a plurality of images, each of which is at least one of a projection image and a reconstructed image of an object, from physical amounts of two or more basis materials included in the first basis material group, wherein at least one of the projection image and the reconstructed image is a multi-energy image, and wherein the reconstructed image is generated from the projection image; and
a second basis material transformation unit that calculates a physical amount of a basis material included in a second basis material group which is different from the first basis material group based on the plurality of images.

2. The image processing device according to claim 1, wherein the image generation unit generates a reconstructed image based on the physical amount of the basis material included in the second basis material group calculated by the second basis material transformation unit.

3. The image processing device according to claim 1, wherein the image generation unit causes a display unit to display the generated images.

4. The image processing device according to claim 1, wherein the image generation unit obtains, by an arithmetic operation, a projection image of a virtual monochromatic X-ray image, wherein the virtual monochromatic X-ray image is a reconstructed image from physical amounts of two or more basis materials, wherein the virtual monochromatic X-ray image is obtained in a case where monochromatic X-rays of a predetermined energy have been radiated, with respect to each of a plurality of monochromatic X-rays of at least two different energies from the physical amounts of the two or more basis materials, and generates images from the respective projection images of virtual monochromatic X-ray images of the at least two different energies, and
wherein the second basis material transformation unit calculates the physical amount of the second basis material included in the second basis material group based on the images generated from the respective projection images of virtual monochromatic X-ray images.

5. An X-ray CT device comprising the image processing device according to claim 1.

6. The image processing device according to claim 1, further comprising a storage unit that stores a photographing condition which has been used to obtain the projection data by photographing and a transformation parameter indicating a relationship between the projection data and the physical amount of the basis material,
wherein the first basis material transformation unit determines a transformation parameter for use in calculating a physical amount of a basis material based on the photographing condition stored in the storage unit, and calculates the physical amount of the basis material with use of the determined transformation parameter.

7. The image processing device according to claim 6, wherein the photographing condition includes information about at least one of an X-ray tube voltage, an X-ray tube current, an X-ray irradiation range, a focus size, a type of an X-ray filter, a type of a bowtie filter, and a photographing time, which have been used to obtain the projection data by photographing.

8. An image processing method comprising:
a first basis material transformation step of calculating each of physical amounts of two or more basis materials included in a first basis material group based on two or more types of projection data different in energy distribution;
an image generation step of generating a plurality of images, each of which is at least one of a projection image and a reconstructed image of an object, from physical amounts of two or more basis materials included in the first basis material group, wherein at least one of the projection image and the reconstructed image is a multi-energy image, and wherein the reconstructed image is generated from the projection image; and
a second basis material transformation step of calculating a physical amount of a basis material included in a second basis material group which is different from the first basis material group based on the plurality of images.

\* \* \* \* \*